(12) United States Patent
Deng

(10) Patent No.: US 10,073,029 B2
(45) Date of Patent: Sep. 11, 2018

(54) SAMPLE MEASUREMENT POOL

(71) Applicant: SUZHOU TAOSPEC OPTRONICS CO., LTD., Suzhou (CN)

(72) Inventor: Wenping Deng, Suzhou (CN)

(73) Assignee: SUZHOU TAOSPEC OPTRONICS CO., LTD., Suzhou (CN)

( * ) Notice: Subject to any disclaimer, the term of this patent is extended or adjusted under 35 U.S.C. 154(b) by 0 days.

(21) Appl. No.: 15/536,624

(22) PCT Filed: Dec. 16, 2015

(86) PCT No.: PCT/CN2015/097540
§ 371 (c)(1),
(2) Date: Jun. 16, 2017

(87) PCT Pub. No.: WO2016/095816
PCT Pub. Date: Jun. 23, 2016

(65) Prior Publication Data
US 2018/0113065 A1 Apr. 26, 2018

(30) Foreign Application Priority Data
Dec. 17, 2014 (CN) .......................... 2014 1 0782027

(51) Int. Cl.
*G01N 21/01* (2006.01)
*G02B 17/00* (2006.01)
*G01N 21/17* (2006.01)

(52) U.S. Cl.
CPC ............. *G01N 21/01* (2013.01); *G01N 21/17* (2013.01); *G02B 17/004* (2013.01)

(58) Field of Classification Search
CPC ............... G01N 21/9501; G01N 21/39; G01N 2201/06113; G01N 2021/95676;
(Continued)

(56) References Cited

U.S. PATENT DOCUMENTS 5,973,864 A * 10/1999 Lehmann ............... G01J 3/42
359/834
6,795,190 B1 * 9/2004 Paul .......................... G01J 3/42
356/437
(Continued)

FOREIGN PATENT DOCUMENTS

CA        2 510 830 A1    7/2004
CN        201269853 Y     7/2009
(Continued)

OTHER PUBLICATIONS

International Search Report, dated Mar. 1, 2016, for International Application No. PCT/CN2015/097540, 4 pages.

*Primary Examiner* — Michael P Stafira
(74) *Attorney, Agent, or Firm* — Seed IP Law Group LLP

(57) ABSTRACT

A sample measurement pool comprises a reflecting cavity and at least one reflecting structure, wherein the reflecting cavity is configured to accommodate a sample to be measured; the reflecting structure is arranged at a boundary of the reflecting cavity; and the reflecting structure comprises a contact surface in contact with the sample to be measured, and a reflecting surface away from the sample to be measured. The sample contact surface has a chemical inertness to the sample, and meanwhile, the surface away from the sample to be measured serve as the reflecting surface, so that the sample to be measured and impurities therein are prevented from damaging the reflecting surface having a reflection function. The sample measurement pool has the advantages of a long optical path and high environmental adaptability.

14 Claims, 8 Drawing Sheets

(58) Field of Classification Search
CPC ...... G01N 21/05; G01N 21/21; G01N 21/956; G01N 15/0227; G01N 2015/0053; G01N 2021/391; G01N 2021/399; G01N 21/031; G01N 21/0317
See application file for complete search history.

(56) References Cited

U.S. PATENT DOCUMENTS

| | | | |
|---|---|---|---|
| 2007/0002922 A1 | 1/2007 | McDonald | |
| 2007/0242720 A1* | 10/2007 | Eckles | G01N 21/031 372/107 |
| 2012/0170112 A1* | 7/2012 | Sandstrom | G02B 7/1815 359/347 |
| 2014/0347662 A1* | 11/2014 | Hodges | G02B 26/001 356/326 |
| 2016/0231239 A1* | 8/2016 | Kotidis | G01N 21/39 |

FOREIGN PATENT DOCUMENTS

| | | |
|---|---|---|
| CN | 201289459 Y | 8/2009 |
| CN | 204314209 U | 5/2015 |
| CN | 204314210 U | 5/2015 |

\* cited by examiner

SAMPLE MEASUREMENT POOL

The present application claims the priority of the Chinese patent application No. 201410782027.0 filed on Dec. 17, 2014 and with the title of "Sample Measurement Pool", which is incorporated herein in its entirety as reference.

TECHNICAL FIELD

The present invention relates to a sample measurement pool, and more particularly, to a sample measurement pool for measuring physicochemical properties of a sample via an optical method.

BACKGROUND

At present, it is required to adopt an absorption spectrometry method to detect micro-samples with the concentration levels of ppm and ppb in the application of many fields. In order to improve the detection sensitivity of the absorption spectrum technology for a low-concentration sample, lengthening an optical path of light beams passing through a sample is an effective method. Obviously, if it merely keeps a light source away from a detector to allow the light beams to pass through a very long and straight transmission-type sample measurement pool, shortcomings of bulky devices, complex collimation and poor temperature stability and anti-vibration performance will be caused. In general, a "folded" optical path is adopted. That is, the optical path is repeatedly reflected between reflecting mirrors to lengthen the effective optical path in a smaller spatial region. For example, White sample pools and Herriott sample pools are the more common ones. Each of them adopts a concave spherical reflecting mirror to repeatedly reflect the optical path in the smaller spatial region. Likewise, there is also a way of adopting a plane reflecting mirror. For instance, a U.S. Pat. No. 3,524,066 describes a technical solution that two plane reflecting mirrors are mounted at two ends of a cylindrical cavity to achieve multiple reflections of the optical path.

However, in practical use, if a test environment is poor (due to excessive dust, corrosive substances, high humidity and temperature, vibration, etc.), in a reflecting mirror-based sample measurement pool, as the front surface is plated with a high-reflecting film (that is, a reflecting film is plated outside the mirror), a reflecting surface and a contact surface in contact with a sample of a reflecting mirror are overlapped; that is, they are the same surface. In practice, the high-reflecting film is in direct contact with the sample in the sample pool, such that the film is likely to be damaged from the sample and impurities therein.

In general, the high-reflecting film is a metal reflecting film or a dielectric reflecting film. If it is the former, the high-reflecting film is very likely to be scratched due to lower metal film hardness of the single-layer metal film. Thus, it is often required to plate the metal film with a protective film. Therefore, the obtained metal reflecting film typically comprises multiple films as the metal reflecting film itself is made via several times of plating. Similarly, if it is the dielectric reflecting film, the obtained dielectric reflecting film also comprises multiple films as the dielectric reflecting film itself is typically made via several times of plating. No matter it is the metal reflecting film or the dielectric reflecting film, when being located in a poor environment with high temperature and humidity, excessive dust, corrosive substance, etc., the high-reflecting film is likely to be damaged since gas, water vapor and impurities in the environment are easy to enter into spaces between every two films of the high-reflecting film and a junction of the high-reflecting film and a glass substrate arising out of limited adhesion between every two films and between the film and a substrate material, and compactness of the films. Moreover, in a preparation process of the high-reflecting film, granular foreign matter is always introduced, resulting in defects in the high-reflecting film. If the reflecting mirror whose film is defective is located in the poor environment, a damaging effect will be exacerbated. As a result, not only are the reflectivity of the high-reflecting film reduced and light energy wasted, but also a film peeling off in a damaged process may block the optical path, further reducing the light energy collection efficiency. What's worse, the glass is deformed and broken under a stress effect of the high-reflecting film, resulting in poor environmental adaptability of the sample measurement pool based on the film-plated reflecting mirror, so that the sample measurement pool cannot adapt to different measurement environments or cannot be normally used in the poor environments.

SUMMARY

An object of the present invention is to provide a sample measurement pool.

A measurement method adopted in the sample measurement pool of the present invention is an optical method including, but not limited to, an absorption spectroscopy method, a Raman spectroscopy method, a scattering spectroscopy method, a fluorometry method, and other analysis methods.

In order to achieve one of the above objects of the present invention, an embodiment of the present invention provides a sample measurement pool. The sample measurement pool comprises a reflecting cavity and at least one reflecting structure; the reflecting cavity is configured to accommodate a sample to be measured; the at least one reflecting structure is arranged at a boundary of the reflecting cavity; the reflecting structure comprises a contact surface and a reflecting surface; the contact surface is in contact with the sample to be measured; the reflecting surface is away from the sample to be measured; at least one of the contact surface and the reflecting surface is a non-planar surface; after multiple reflections, incident light forms an optical measuring path in the reflecting cavity; the incident light enters the reflecting cavity through an incident portion where the incident light is in contact with the optical measuring path for the first time; and the incident portion and the reflecting surface are arranged in a discontinuous manner.

As an improvement of an embodiment of the present invention, the reflecting structure is a reflecting mirror, and the sample measurement pool comprises at least two reflecting mirrors arranged at the two ends of the reflecting cavity, respectively.

As a further improvement of an embodiment of the present invention, the reflecting cavity is a region formed by the optical measuring path.

As a yet further improvement of an embodiment of the present invention, the reflecting surface is plated with a reflecting film.

As a yet further improvement of an embodiment of the present invention, the reflecting surface is a full reflecting surface.

As a yet further improvement of an embodiment of the present invention, the incident portion is a light-passing surface or a light-passing hole of the reflecting structure or an incident region around the reflecting structure.

As a yet further refinement of an embodiment of the present invention, the non-planar surface is a spherical surface, a cylindrical surface, a quadratic curve surface, a free-form curve surface or an aspherical surface.

As a yet further improvement of an embodiment of the present invention, the waist position of the incident light is located inside the reflecting cavity.

As a yet further improvement of an embodiment of the present invention, an included angle in a value range of 0°-360° is formed between the at least one reflecting structure.

As a yet further improvement of an embodiment of the present invention, a protective structure is arranged on the reflecting surface, and is configured to protect the reflecting surface.

Compared with the prior art, the present invention has the benefits that one surface away from the sample to be measured serves as the reflecting surface of the reflecting structure, so that the sample to be measured and the impurities therein will not damage the reflecting surface playing a reflection role. In the present invention, the long optical path is provided, and meanwhile, the environmental adaptability of the sample measurement pool is greatly improved, so that the present invention has the advantages of a long optical path and high environmental adaptability.

DETAILED DESCRIPTION

The present invention will be described in detail below with reference to specific embodiments shown in the accompanying drawings. However, these embodiments are not intended to limit the present invention, and changes of structures, methods or functions, made by ordinary person skilled in the art in accordance with these embodiments are included within the protective scope of the present invention.

Figure 1:
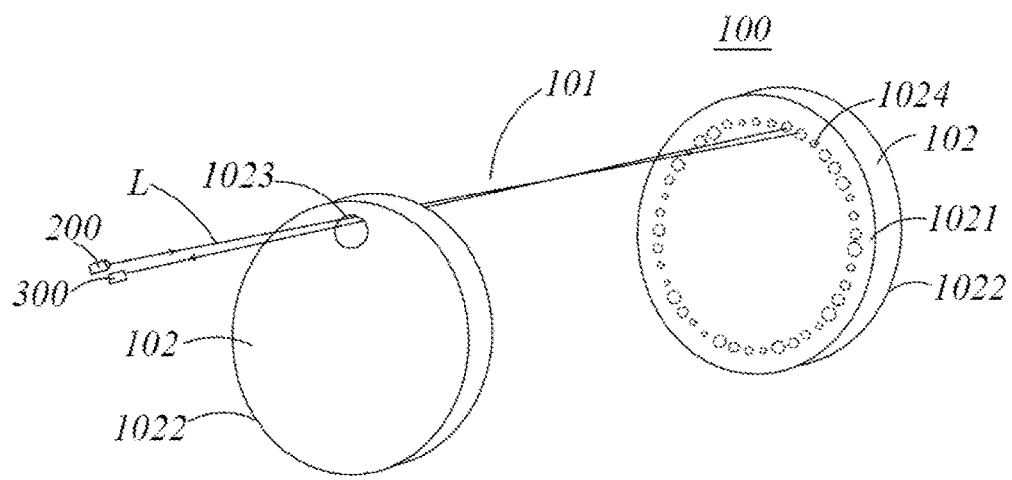
FIG. 1 shows a perspective view of a sample measurement pool according to an embodiment of the present invention.
Figure 2:
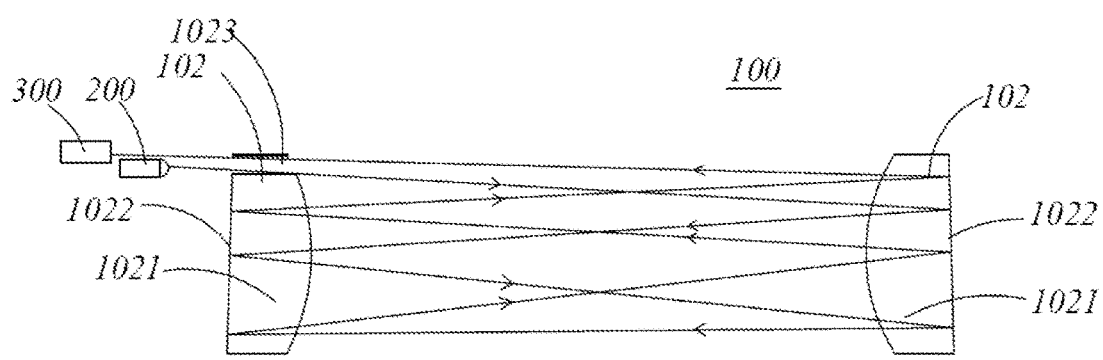
FIG. 2 shows a front view of the sample measurement pool according to an embodiment of the present invention.

As shown in FIGS. 1 and 2, in an embodiment of the present invention, a sample measurement pool 100 comprises a reflecting cavity 101 and one or more reflecting structures 102. The reflecting cavity 101 is configured to accommodate a sample to be measured. The one or more reflecting structures 102 are arranged at boundaries of the reflecting cavity 101. The one or more reflecting structures 102 comprise contact surfaces 1021 and reflecting surfaces 1022; the contact surfaces 1021 are in contact with the sample to be measured; the reflecting surfaces 1022 are away from the sample to be measured, and are not in contact with the sample to be measured; and at least one of the contact surfaces 1021 and the reflecting surfaces 1022 is a non-planar surface. After multiple reflections, incident light L forms an optical measuring path in the reflecting cavity 101; the incident light L enters the reflecting cavity 101 through an incident portion where the incident light L is in contact with the optical measuring path for the first time; and the incident portion and the reflecting surfaces 1022 are arranged in a discontinuous manner.

Here, surfaces in direct contact with the sample to be measured are the contact surfaces 1021, and the reflecting surfaces 1022 for realizing reflection are away from the sample to be measured. That is, the contact surfaces 1021 which do not play a reflection role will be damaged, and the reflecting surfaces 1022 are not affected by the sample to be measured or impurities therein. Thus, the environmental adaptability of the sample measurement pool 100 is greatly improved. Compared with the prior art, enabling the reflecting surfaces 1022 to be away from the sample to be measured has the benefit that the reflecting surfaces 1022 may be provided with a protective structure. For example, the protective structure is a mechanical structure for protecting the reflecting surfaces 10122 from being scratched, and for preventing the reflecting surfaces 022 from being in contact with gas, moisture and other impurities. It is possible to place a desiccant around the reflecting surfaces 1022, or a space between the reflecting surfaces and the mechanical structure may be arranged in a high vacuum state or may be filled with an inert gas or the like. But, the present invention is not limited thereto.

In this embodiment, the reflecting structure 102 is a reflecting minor 102, and the sample measurement pool comprises at least two reflecting mirrors 102, which are arranged at boundaries of the reflecting cavity 101, respectively. As shown in FIG. 1, the incident light L is reflected repeatedly in the reflecting cavity 101, and a total path formed by repeatedly reflected light paths in the reflecting cavity 101 is an optical measuring path in this embodiment which forms the reflecting cavity 101. The incident portion is a light-passing surface or a light-passing hole 1023 of one reflecting mirror 102 or an incident region around the reflecting mirror 102. The incident light L enters the reflecting cavity 101 via the light-passing hole 1023. Here, a portion where the incident light L is in contact with the optical measuring path for the first time is a portion of the light-passing hole 1023. That is, the incident portion is the light-passing hole 1023; and the light-passing hole 1023 and the reflecting surfaces 1022 are arranged in a discontinuous manner. The discontinuous arrangement means surfaces of the light-passing hole 1023 and the reflecting surfaces 1022 are discontinuous surfaces. Moreover, with respect to physical properties of the light-passing hole 1023 and the reflecting surfaces 1022, the former allows light to pass through, while the later reflects the light, such that the physical properties of the light-passing hole 1023 and the reflecting surfaces 1022 are discontinuous, either. In other embodiments, when the incident light L is incident to the reflecting cavity 101 from the side surface of one reflecting mirror 102, the incident portion is an incident region around the reflecting mirror 102, and the incident region around the reflecting mirror is not in contact with the corresponding reflecting surface 1022. That is, the incident portion and the reflecting surface 1022 are arranged in a discontinuous manner.

Figure 3:
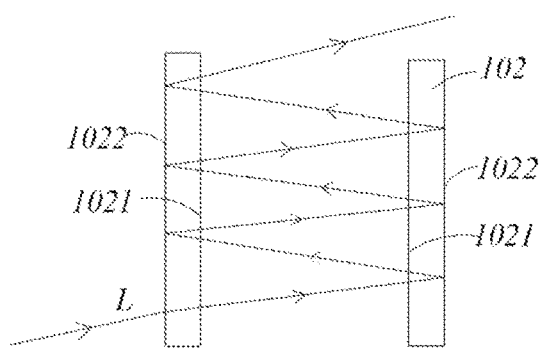
FIG. 3 shows a schematic view of a continuous arrangement according to an embodiment of the present invention.

The discontinuous arrangement is opposite to continuous arrangement. As shown in FIG. 3, the incident light L is directly incident on one reflecting surface 1022, and a portion where the incident light L is in contact with the optical measuring path for the first time is located on the reflecting surface 1022. That is, the incident portion is located on the reflecting surface 1022. Thus, the surfaces of the incident portion and the reflecting surfaces 1022 are continuous surfaces, and the physical properties of the incident portion and the reflecting surface 1022 are continuous. Here, the incident portion and the reflecting surface 1022 are arranged in a continuous manner.

In this embodiment, a material for manufacturing each reflecting mirror 102 may be glass. At present, known available materials include fused silica, sapphire, calcium fluoride, diamond, yttrium aluminum garnet (YAG), Si3N4, ZrO2, Al2O3, HfO2 and other media that are transparent in an optical wave frequency range, but are not limited thereto. As these materials have chemical inertness, when the reflecting mirror 102 made of any of such materials is placed in the sample measurement pool 100, the contact surface 1021 of the reflecting mirror will not be damaged by the sample to be measured in the sample measurement pool 100 and impurities in the sample to be measured. But, it is not limited thereto. For example, the contact surface 1021 is attached with a material which has a chemical inertness to the sample to be measured and the impurities in the sample to be measured.

In the present embodiment, each reflecting surface 1022 is plated with a reflecting film having a high reflectivity. With respect to its material, the reflecting film may be a dielectric film or a metal film, but it is not limited thereto. Compared with the prior art, in the present embodiment, the reflecting film is arranged on the corresponding reflecting surface 1022, and is not in contact with the sample to be measured and impurities in the sample. When the reflecting mirrors 102 are placed in a sample measurement pool 100 with high temperature and humidity, excessive dust, and corrosive substance, a sample to be measured in the sample measurement pool 100 and impurities in the sample will not enter inside the reflecting films or junctions of the reflecting films and the reflecting surfaces 1022, so that a reflecting performance of the reflecting film will not be affected. Therefore, the reflecting mirrors 102 of the present embodiment are suitable for poor environment (with excessive dust, corrosive substance, high humidity, high temperature, etc.). In addition, an incident light L in the present embodiment enters the reflecting cavity 101 through an incident portion. When the incident light L satisfies a certain incident condition, the light is repeatedly reflected within the reflecting cavity 101, so that a longer optical path is obtained. Therefore, the present embodiment has the advantages of a long optical path and high environmental adaptability.

As shown in FIGS. 1 and 2, at least one of the contact surfaces 1021 and the reflecting surfaces 1022 of the at least two reflecting mirrors 102 is a non-planar surface. The non-planar surface may be a spherical surface, a cylindrical surface, a quadratic curve surface, a free-form curve surface or an aspherical surface, but is not limited thereto. The non-planar surface may be determined based on an actual situation.

In the present embodiment, as shown in FIG. 2, the two reflecting mirrors 102 are taken as an example, and the contact surfaces 1021 of the two reflecting mirrors 102 are spherical. An incident portion is arranged at the boundary of the reflecting cavity 101. In this embodiment, a light-passing hole 1023 in one reflecting mirror 102 of the two reflecting mirrors 102 is taken as the incident portion. After the incident light L is incident on the contact surface 1021 of one reflecting mirror 102 in the two reflecting mirrors 102 through the incident portion, as the reflecting mirror 102 is made of a transparent material, the light passes through the contact surface 1021 of the reflecting mirror 102 to the reflecting surface 1022, then is reflected repeatedly by the reflecting surfaces 1022, and finally is emitted from the light-passing hole 1023. Referring to FIG. 2, as the contact surface 1021 is spherical, light spots obtained after multiple reflections are generally distributed in a closed manner. That is, the incident light L and the emergent light share the same light-passing hole 1023 for incoming and outgoing, so that after multiple reflections, light spots 1024 of the emergent light are overlapped with, adjacent to or separated by several light spots from those of the incident light L. The distribution of the light spots 1024 and a position relationship between the light spots 1024 of the emergent light and the light spots 1024 of the incident light are determined depending on an actual situation. When the incident light L and the emergent light share the same light-passing hole 1023 for incoming and outgoing, the stability of the sample measurement pool 100 can be improved, and moreover, the size of the sample measurement pool 100 can be reduced.

Figure 4:
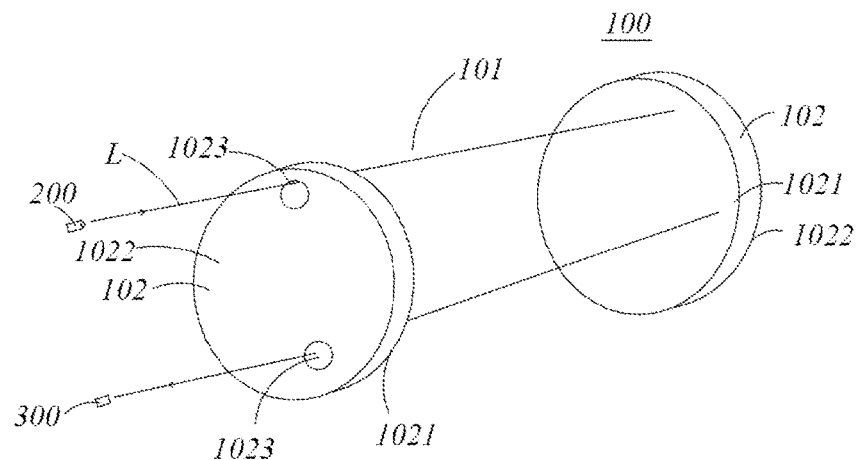
FIG. 4 shows a schematically structural view of a light-passing hole according to an embodiment of the present invention.
Figure 5:
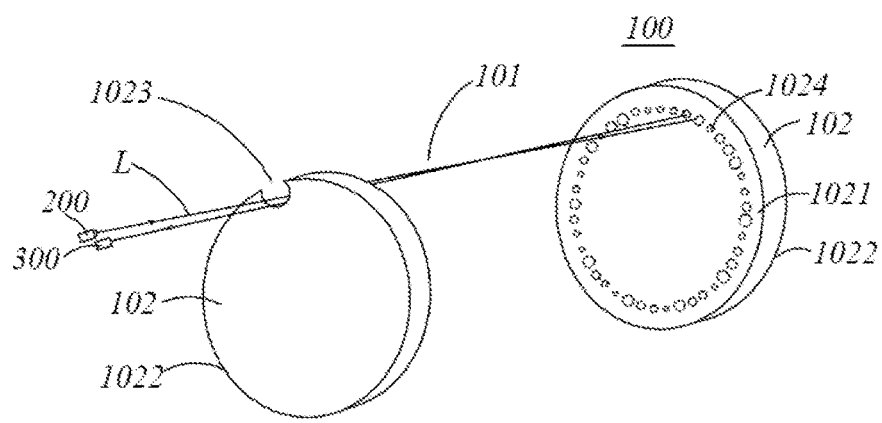
FIG. 5 shows a schematically structural view of the light-passing hole according to another embodiment of the present invention.

In the present embodiment, each of the two reflecting mirror 102 may be provided with a light-passing hole 1023. The number of the light-passing hole 1023 may be one or more. As shown in FIG. 4, for example, a plurality of light-passing holes 1023 are formed in one reflecting mirror 102, such that incoming of the incident light L and outgoing of the emergent light may be realized via the different light-passing holes 1023. The positions of the light-passing holes 1023 are not limited in the middle of the reflecting mirror 102. As shown in FIG. 5, the light-passing hole 1023 may be formed in the edge of one of the reflecting mirrors 102. That is, the light-passing hole 1023 can penetrate through the edge of the reflecting mirror 102. Here, the light-passing hole 1023 is a non-closed hole. The reflecting mirror 102 may not be provided with a light-passing hole 1023. For example, the incident light L is incident upon the reflecting cavity 101 from a side of the reflecting mirror 102.

In the present embodiment, as the light will enter the inside of the reflecting mirror 102 in a propagation process, if the design is improper, reflected light on the surface of the reflecting mirror 102 may interfere with a main optical path formed by the incident light L, resulting in low detection sensitivity. Experiment results show that the nature of the problem is that the reflecting mirror 102 is equivalent to a parallel plane cavity; and if the parallelism is destroyed, the influence of the reflected light on the surface of the material on the main optical path can be reduced. Thus, in this embodiment, at least one of the contact surfaces 1021 and the reflecting surfaces 1022 of the at least two reflecting mirrors 102 is arranged as a non-planar surface, such as a spherical surface, a cylindrical surface, a quadratic curve surface, a free-form curve surface or an aspherical surface, but is not limited thereto. Thus, when the incident light L is incident on the reflecting surface 1022, an included angle is formed between the reflected light and the incident light L, so that interference of light in a reflecting process on the main optical path formed by the incident light L is prevented, reducing stray light in the sample measurement pool 100. It is known from the computer simulation experiments that in a case that other influence factors are the same, the smaller the curvature radius of the non-planer surface is, the less the influence of the reflected light on the surface of the reflecting mirror 102 on the main optical path will be. Through reasonable selection of the curvature radius, the influence of the reflected light on the surface of the reflecting mirror 102 on the main optical path can be effectively avoided. In addition, at least one of the contact surfaces 1021 and the reflecting surfaces 1022 of the at least two reflecting mirrors 102 is arranged as a non-planar surface; and the size of a light spot 1024 will be gradually increased along with the increase of a propagation distance as the actual light spot 1024 of the incident light L has a certain divergence angle, and the set non-planer surface is equivalent to a convergent lens, so that the size of the light spot 1024 is reduced, and a divergence angle of the incident light L is restricted.

For example, the incident light L is emitted by a collimator in the present embodiment, and a light spot 1024 emitted from the collimator has a certain divergence angle. Parameters of a light source 200 and the collimator determine a change relationship between the sizes of light spots 1024 and propagation distances. The sizes of the light spots 1024 will be decreased first and then increased along with the increase of the propagation distance or will be increased along with the increase of the propagation distance, and the position of the minimum light spot 1024 is called a waist position. In order to make the light spots 1024 distributed on the reflecting mirror 102 smaller, in this embodiment, the waist position of the light spots 1024 is arranged inside the reflecting cavity 101. That is, the position of the minimum light spot 1024 of the incident light L is located inside the reflecting cavity 101. As the reflecting cavity 101 is symmetrical, when the waist position is located inside the reflecting cavity 101, the light spots 1024 will repeatedly pass through a process of "convergence-divergence-convergence-divergence", enabling the sizes of the all light spots 1024 on the reflecting mirror 101 to be smaller. Therefore, by arranging the waist position inside the reflecting cavity 101, an effect that the light spots 1024 on the reflecting mirror 102 are smaller is realized, further improving the surface utilization ratio of the reflecting mirror 102.

Figure 6:
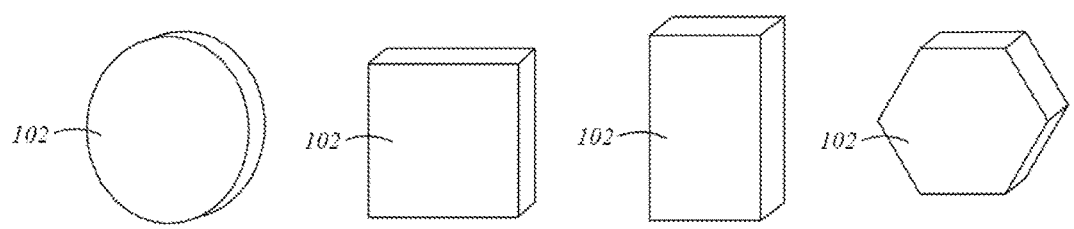
FIG. 6 shows a schematic view of the shape of a reflecting mirror according to an embodiment of the present invention.

In the present embodiment, the shape of the reflecting mirror 102 is not limited. For example, as shown in FIG. 6, it may be circular, square, polygonal, or the like. The non-planar surface form of the reflecting mirror 102 is not limited. For instance, it may be a spherical surface, a cylindrical surface, a quadratic curve surface, a free-form curve surface, an aspherical surface or the like, but is not limited thereto. The arrangement positions of the reflecting mirrors 102 are not limited. That is, a distance, an angle or other relationships between the reflecting mirrors 102 may be determined according to an actual situation. For example, there may be an included angle between the reflecting mirrors 102. Moreover, the number of the reflecting mirrors 102 is not limited. The number of reflecting mirrors 102 constituting the sample measurement pool 100 may be more than two, and the reflecting mirrors 102 may be arranged as an arrayed device. For example, if there are multiple reflecting mirrors 102, they may be distributed on a circumference, but the case is not limited thereto. The sizes of the reflecting mirrors 102 are not limited. For example, the sizes of the reflecting mirrors 102 in the same sample measurement pool 100 may be different. The reflecting mirrors 102 may cooperate with other components, such as a prism. The multiple reflecting mirrors 102 may also be arranged as a whole. The realization of the incoming and outgoing of the incident light L is not limited to the light-passing hole 1023. For example, the incoming and outgoing of the incident light L may be realized from the sides of the reflecting mirrors 102.

Figure 7:
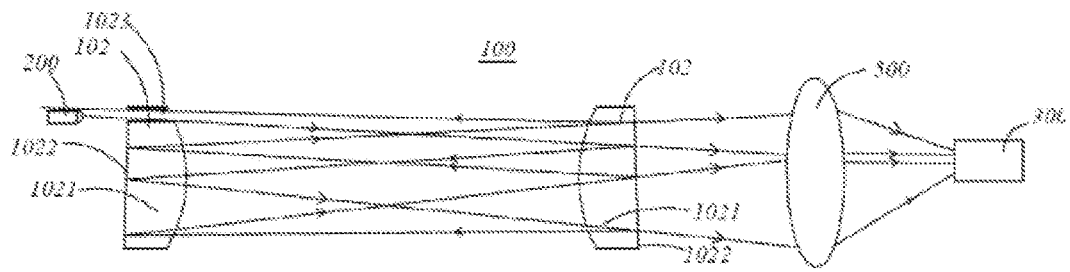
FIG. 7 shows a schematically structural view of a detector according to an embodiment of the present invention.

As shown in FIG. 7, the sample measurement pool 100 provided by the present embodiment further comprises a detector 300 and a light source 200. The light source 200 is configured to emit an incident light L. The detector 300 is configured to receive the light emitted from the sample measurement pool 100. The light emitted from the sample measurement pool 100 can be converged into the detector 300 via a lens 500 every time. For example, a sample to be measured may be a solid, gas, liquid, liquid crystal, biological tissue and the like, but is not limited thereto.

Figure 8:
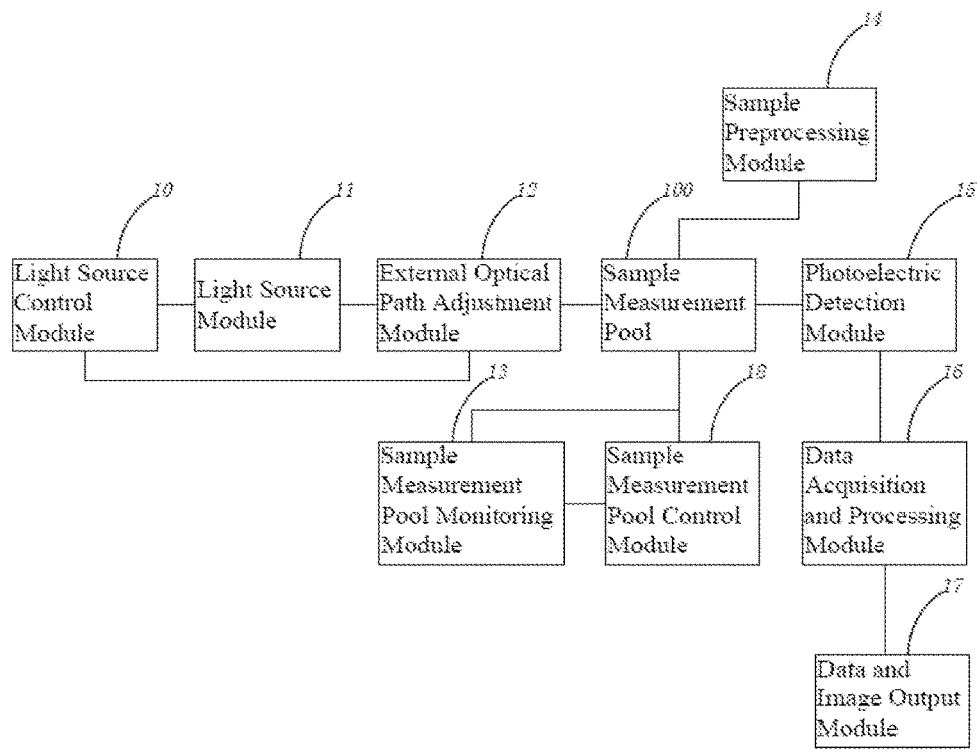
FIG. 8 is a measurement flow module diagram of the sample measurement pool according to an embodiment of the present invention.

A measurement flow module diagram of the sample measurement pool 100 provided by the present invention is shown in FIG. 8, and includes, but is not limited to, a light source control module 10, a light source module 11, an external optical path adjustment module 12, the sample measurement pool 100, a sample measurement pool monitoring module 13, a sample measurement pool control module 18, a sample preprocessing module 14, a photoelectric detection module 15, a data acquisition and processing module 16, and a data and image output module 17. It should be specially noted that the number of each module shown in FIG. 8 can be appropriately increased or decreased according to an actual measurement demand. If the sample to be measured does not require preprocessing, the sample preprocessing module 14 may be omitted.

A working principle or function of each module in this embodiment is as follows.

The light source control module 10 is configured to control functions such as on/off, frequency modulation, current tuning and temperature tuning of the light source module 11.

The light source module 11 may have different forms according to different detection technologies and use requirements, and includes but is not limited to a laser light source, a broadband light source, a combination of laser light sources different in frequency, a combination of the laser light source and the broadband light source, and the like.

The external optical path adjustment module 12 is configured to change a polarization property of light, a divergence angle of a light beam, energy distribution of a light field, and the like, and to feed back a signal to the light source control module 10. The external optical path adjustment module 12 includes, but is not limited to a polarizing device, an optical coupling device, a light cutting device, and the like.

The sample measurement pool 100 is an optical delay system, and is configured to lengthen a light propagation path and an optical path to improve the system measurement sensitivity. The sample measurement pool 100 includes, but is not limited to a multiple-reflection cavity, an optical resonance cavity, and the like.

The sample measurement pool monitoring module 13 is configured to monitor a working state of the reflecting cavity 101, to perform fault alarm, to really-timely calibrate an equivalent absorption optical path of the sample measurement pool 100 on line, and to provide a monitoring signal to the sample measurement pool control module 18.

The sample measurement pool control module 18 is configured to real-timely correct a relative position relationship of optical devices in the sample measurement pool 100 on line according to the monitoring signal provided by the sample measurement pool monitoring module 13, and includes, but is limited to at least one PZT or other mechanical structures or devices with a translational rotation function or a combination thereof. Through the sample measurement pool control module 18, the relative position relationship of the optical devices in the sample measurement pool 100 can be changed.

The sample preprocessing module 14 is configured to preprocess the sample to be measured. The functions of the sample preprocessing module 14 include, but are not limited to heating the sample to be measured, filtering out moisture in the sample, removing other impurities irrelevant to measurement in the sample, filtering out dust, and the like.

The photoelectric detection module 15 is configured to receive and detect an optical signal output from the sample measurement pool 100, to convert the optical signal into an electrical signal, and to perform processing such as filtration, amplification and analog-to-digital conversion on the signal.

The data acquisition and processing module 16 is configured to acquire a converted photoelectric digital signal and to perform spectral signal processing such as average and concentration calculation.

The data and image output module 17 is configured to output data and image information such as a spectral line, molecular spectral absorption intensity and a concentration value of a sample. It should be noted that the data and image output module 17 is arranged to display information such as element concentration, and is free from form and structure limitation.

The sample measurement pool 100 provided by the present invention may be embodied in various embodiments according to different specific situations referring to the number, location, form and the like of the reflecting structure 102. Other embodiments of the present invention will be described in detail below. However, the embodiments of the present invention are not limited to these specific examples. To simplify the description, a part of components have been omitted, and the same components have the same reference numbers.

Figure 9:
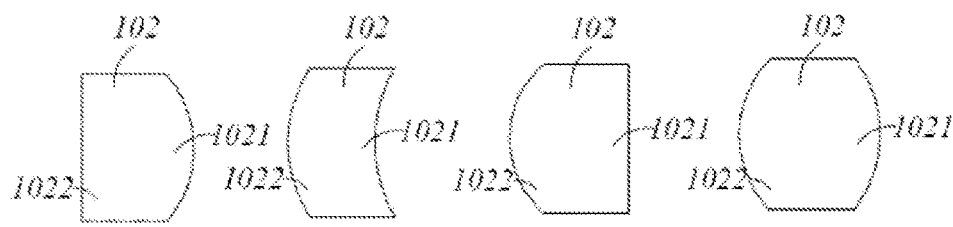
FIGS. 9-20 show schematically structural views of other embodiments of the present invention.
Figure 10:
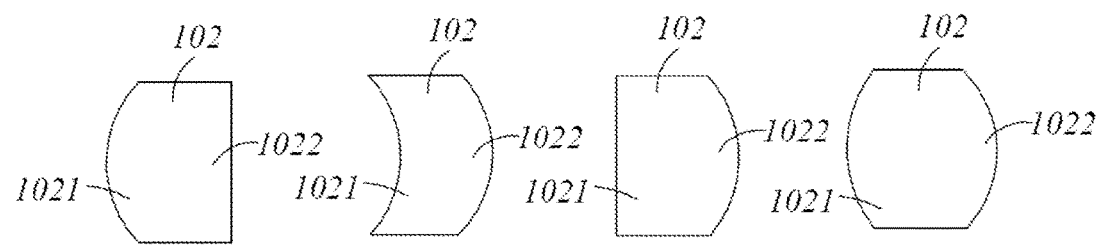

As shown in FIGS. 9 and 10, in this embodiment, the sample measurement pool 100 comprises two reflecting minors 102, one of which may be any one reflecting mirror 102 shown in FIG. 9, and the other may be any one reflecting minor 102 shown in FIG. 10. The reflecting mirror may be arbitrarily combined according to actual needs.

Figure 11:
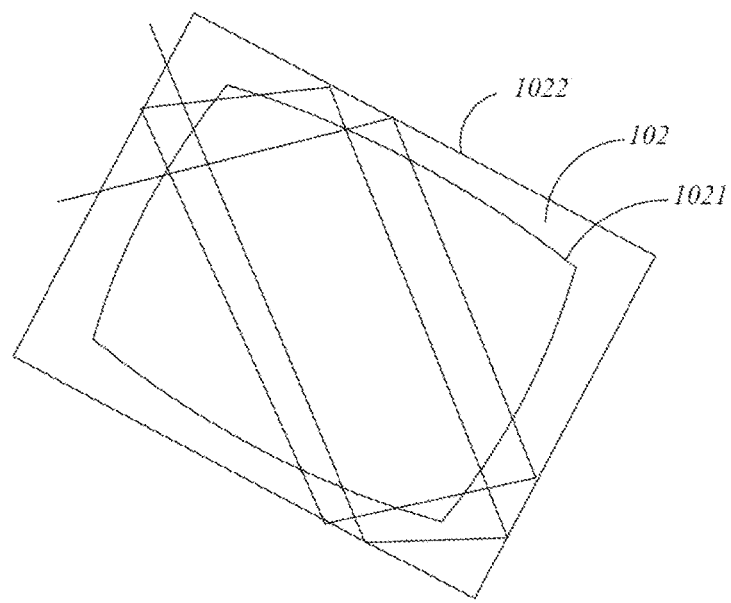
Figure 12:
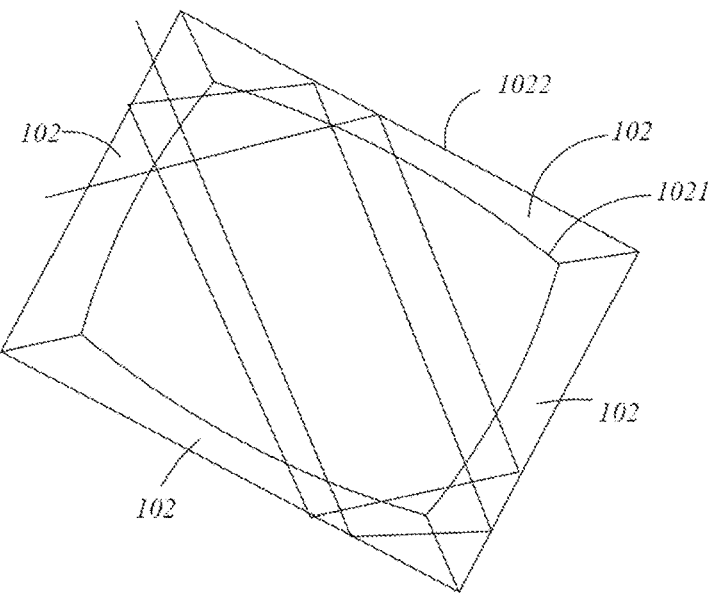

As shown in FIG. 11, in this embodiment, the sample measurement pool 100 comprises a reflecting mirror 102 in a shape of a square ring. Here, an intermediate portion of the square-ring-shaped reflecting mirror 102 forms a reflecting cavity 101; a contact surface 1021 of the reflecting mirror 102 is a non-planar surface; and an incident light L enters the reflecting cavity 101 and passes through the contact surface 1021 to be reflected back and forth at the reflection surface 1022, so that an area utilization ratio of the reflection surface 1022 playing the reflection role is increased, and an optical path is lengthened as the light repeated reflection times are increased. In another embodiment, as shown in FIG. 12, the square-ring-shaped reflecting mirror 102 may be stitched by a plurality of reflecting mirrors 102.

Figure 13:
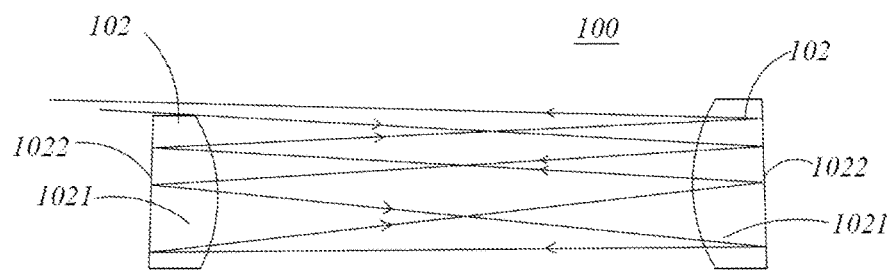

As shown in FIG. 13, in this embodiment, the sample measurement pool 100 comprises two reflecting mirrors 102. Contact surfaces 1021 of the two reflecting minors 102 in this embodiment are arranged as non-planar surfaces. One reflecting minor 102 is smaller than the other reflecting mirror 102. Thus, the incident light L can enter from a non-overlapping portion of the two reflecting minors 102.

Figure 14:
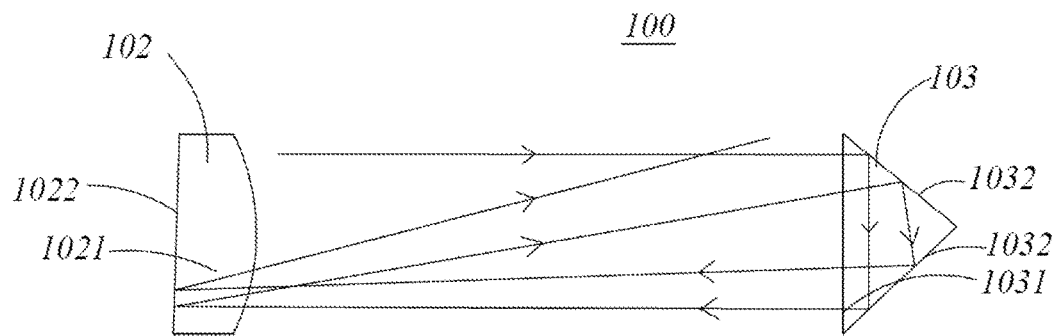

As shown in FIG. 14, in this embodiment, the sample measurement pool 100 comprises a reflecting mirror 102 and a prism 103. A contact surface 1021 of the reflecting mirror 102 is a non-planar surface; and the reflecting surface 1032 of the prism 103 is a full reflecting surface. An incident light L enters the prism 103 at a predetermined angle, such that the light can be fully reflected at the reflecting surface 1032 of the prism 103. Of course, the reflecting surface 1032 of the prism 103 may be plated with a reflecting film to improve a reflecting effect. The prism 103 may be a right-angled prism, a pyramid prism, an isosceles prism and the like, but is not limited thereto. The type of the prism 103 may be determined depending on an actual situation.

Figure 15:
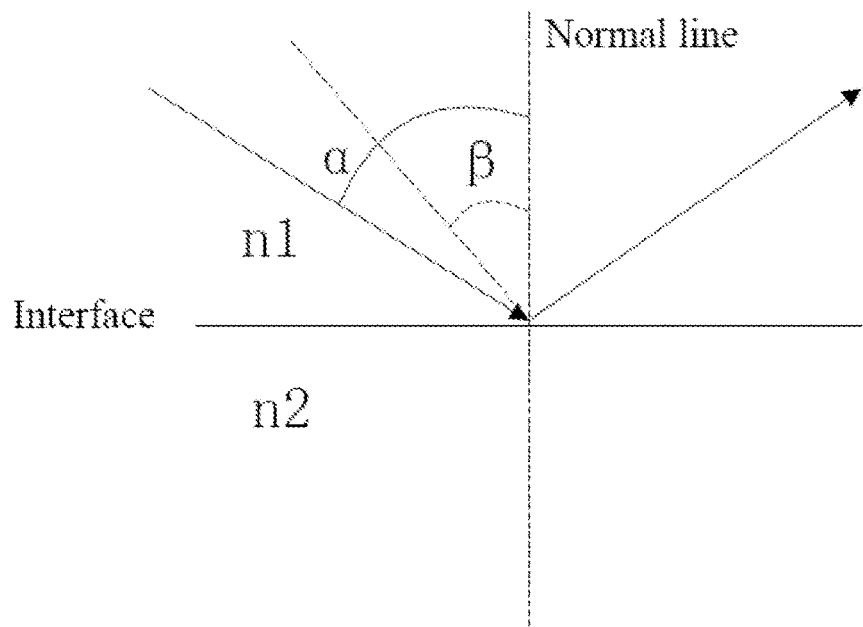

As shown in FIG. 15, in this embodiment, light is incident from an optical density medium (with a refractive index of n1) to an optical sparse medium (with a refractive index of n2, and n1>n2). If an incident angle α is greater than a critical angle β (β=arcsin (n2/n1)), light is fully reflected back to the optical density medium. Here, this condition is called as a full reflection condition, and this phenomenon is called as a full reflection. An interface between the optical density medium and the optical sparse medium is referred to as a full reflecting surface, and the full reflecting surface of the above embodiment is the reflecting surface 1032 of the prism 103.

Figure 16:
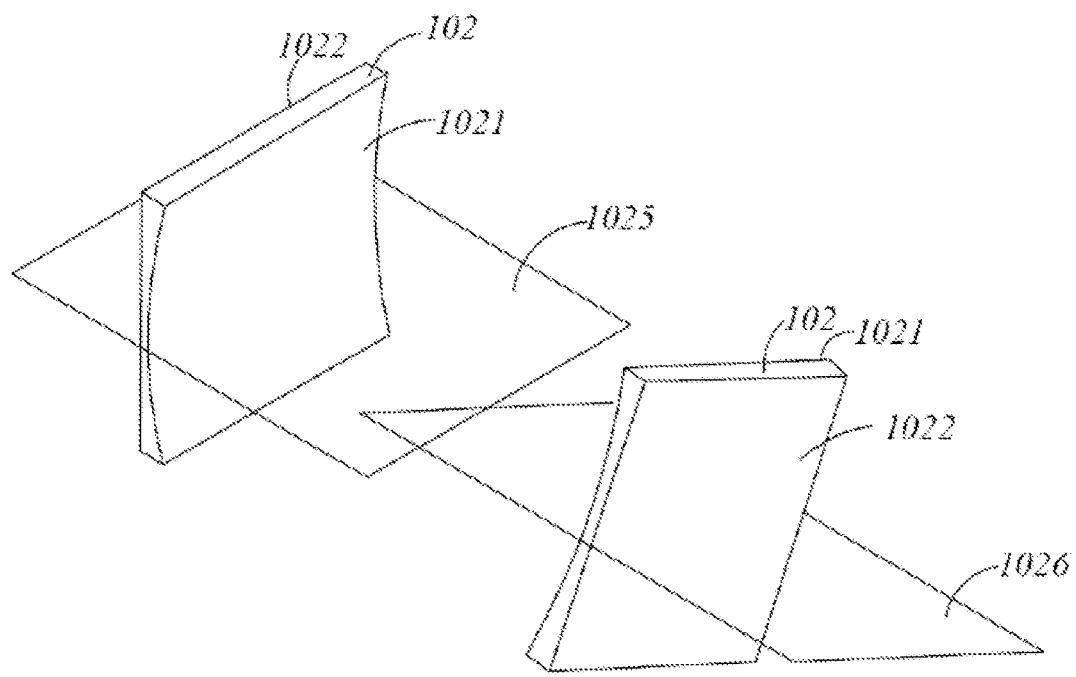
Figure 17:
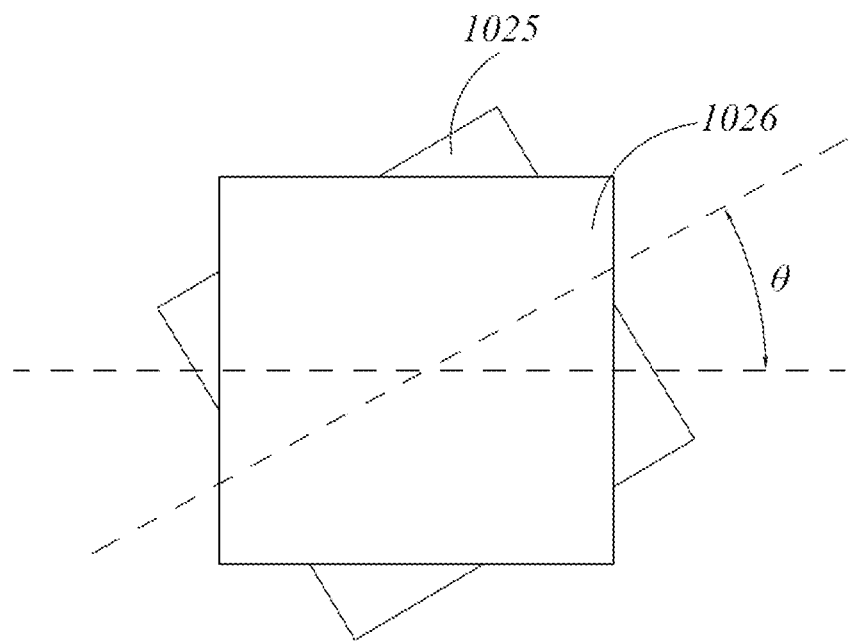

As shown in FIG. 16, in this embodiment, the sample measurement pool 100 comprises two reflecting mirrors 102. Contact surfaces 1021 of the reflecting mirrors 102 are non-planar surfaces which may be, for example, spherical surfaces, cylindrical surfaces, quadratic curve surfaces, freeform curve surfaces or aspherical surfaces, but are not limited thereto. Each reflecting mirror 102 is square, but is not limited thereto. A light-passing hole is formed in at least one reflecting mirror of the two in the two reflecting mirrors 102. An included angle between the two reflecting mirrors 102 is θ whose value range is in 0°-360° (including 0°). Through angle adjustment, a light propagation path can be controlled, such that the generality of the sample measurement pool 100 is higher, and available areas of reflecting surfaces of the reflecting mirrors 102 are larger. It is defined that an angle between maximum curvature radius planes of the reflecting surfaces 1022 is the included angle, namely, a dihedral angle. As shown in FIGS. 16 and 17, the maximum curvature radius plane of one reflecting mirror 102 in the two reflecting mirrors 102 is a first plane 1025; the maximum curvature radius plane of the other reflecting mirror 102 in the two reflecting mirrors 102 is a second plane 1026; and the included angle between the first plane 1025 and the second plane 1026 is θ.

Figure 18:
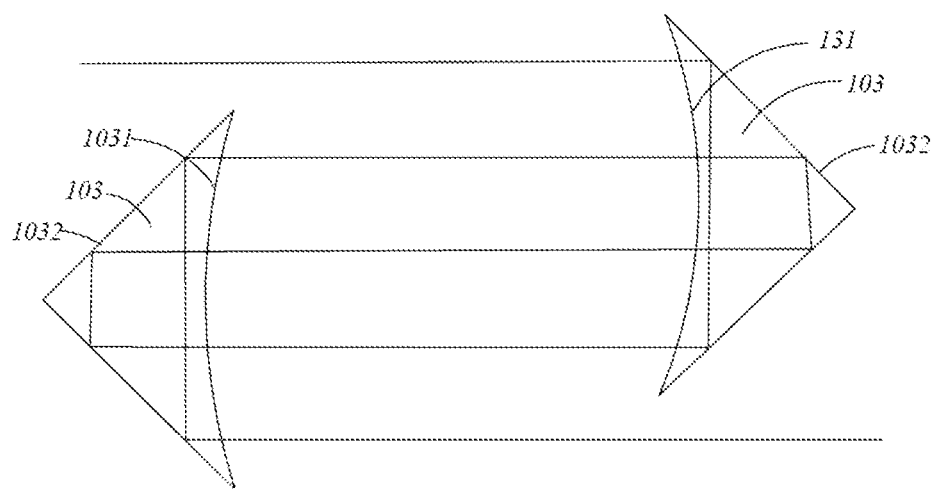

As shown in FIG. 18, in this embodiment, the sample measurement pool 100 comprises two right-angle prisms 103. Each right-angle prism 103 comprises a contact surface 1031 and a reflecting surface 1032. The contact surfaces 1031 are non-planar surfaces, while the reflecting surfaces 1032 are full reflecting surfaces. The incident light L can be fully reflected at the reflecting surfaces 1032 to realize light reflection back and forth. The two right angle prisms 103 are arranged in a staggered manner, so that a range of the reflecting cavity 101 can be wider. However, this embodiment is not limited thereto. For example, the sample measurement pool 100 may include two pyramid prisms or isosceles prisms. In addition, the incident light can be incident on the contact surface 1031 at a certain angle, such that the light can be spirally propagated in the reflecting cavity 101.

Figure 19:
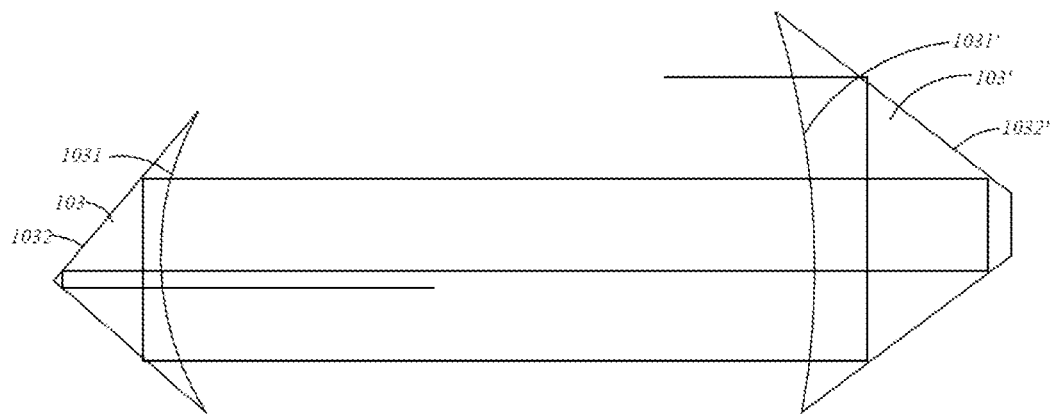

As shown in FIG. 19, in this embodiment, the sample measurement pool 100 comprises a right-angle prism 103 and a non-right-angle prism 103' which are different from each other in size. The right-angle prism 103 comprises a contact surface 1031 and a reflecting surface 1032, while the non-right-angle prism 103' comprises a contact surface 1031' and a reflecting surface 1032'. The contact surfaces 1031 and 1031' are non-planar surfaces, and the reflecting surfaces 1032 and 1032' are full reflecting surfaces. The incident light may be fully reflected at the reflecting surfaces 1032 and 1032' to realize multiple reflections of light.

Figure 20:
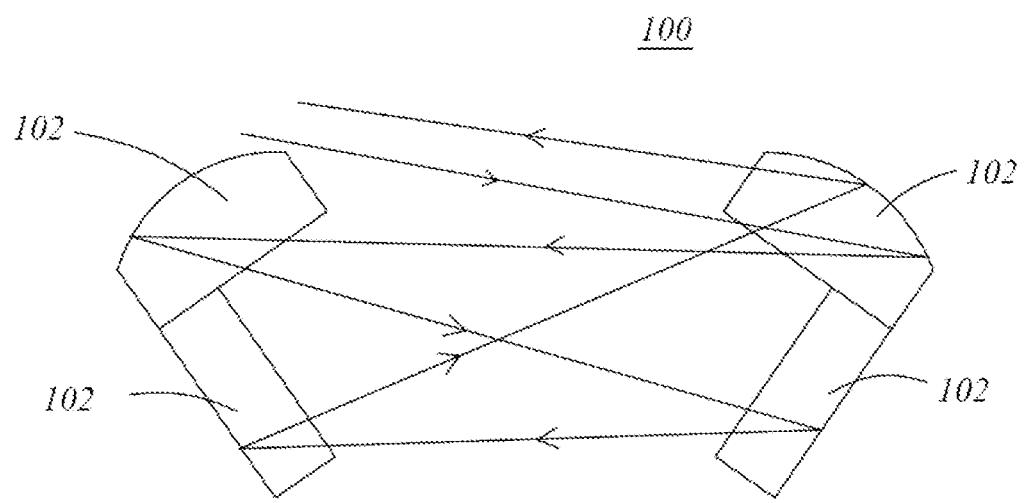

As shown in FIG. 20, in this embodiment, the sample measurement pool 100 comprises four reflecting mirrors 102, every two of which are combined into a whole. When the incident light L is incident in a specific incident manner, the light may be spirally propagated in the sample measurement pool 100, so that the utilization ratio of the reflecting surfaces is improved, and a long optical path is obtained. The sample measurement pool 100 may also comprise six reflecting mirrors 102, every three of which are combined. The every three reflecting mirrors 102 may be stitched in a mutually perpendicular manner or combined into a whole, so that three mutually perpendicular contact surfaces 1021 and corresponding mutually perpendicular reflecting surfaces 1022 are formed. The light may be reflected back and forth between the mutually perpendicular reflecting surfaces 1022, such that the areas of the reflecting surfaces 1022 playing a reflection role are increased, increasing repeated reflection times, and lengthening the optical path.

In other embodiments, the type of the sample measurement pool 100 may be in other forms, such as a Robert-type sample measurement pool, a White sample measurement pool, and the like. Other specific structures will not be repeated herein.

In conclusion, the reflecting structure 102 provided by the present invention replaces a conventional reflecting structure with an externally plated reflecting film. As the reflecting surface 1022 of the reflecting structure 102 is away from the sample to be measured and is not in contact with the sample to be measured, a problem of poor environmental adaptability of the conventional reflecting structure with the externally plated reflecting film is solved. In the present invention, not only is long optical path provided, but also the environmental adaptability of the sample measurement pool 100 is greatly improved, so that the present invention has the advantages of a long optical path and high environmental adaptability. In the present invention, through reasonable selection of the curvature radius of the non-planar surface, stray light in the sample measurement pool 100 is effectively reduced. According to the present invention, the distribution of the light spots on the reflecting structure 102 can be closed, improving the stability and realizing miniaturization. In the present invention, the waist position of the light spots 1024 is arranged inside the reflecting cavity 101, so that the size of the light spots 1024 on the reflecting structure 102 is optimized, and the surface utilization ratio of the reflecting structure 102 is further increased.

It should be understood that although the description is described based on the embodiments, not every embodiment includes only one independent technical solution. This statement of the description is only for clarity. Those skilled in the art should treat the description as a whole, and technical solutions in all of the embodiments may also be properly combined to form other embodiments that will be understood by those skilled in the art.

The above detailed description only aims to specifically illustrate the available embodiments of the present invention, and is not intended to limit the protection scope of the present invention. Equivalent embodiments or modifications thereof made without breaking away from the spirit of the present invention shall fall within the protection scope of the present invention.

The invention claimed is:

1. A sample measurement pool, comprising: a reflecting cavity configured to accommodate a sample to be measured, and at least one reflecting structure arranged at a boundary of the reflecting cavity, wherein the reflecting structure comprises a contact surface and a reflecting surface; the contact surface is in contact with the sample to be measured; the reflecting surface is away from the sample to be measured; at least one of the contact surface and the reflecting surface is a non-planar surface; after multiple reflections, incident light forms an optical measuring path in the reflecting cavity; the incident light enters the reflecting cavity through an incident portion where the incident light is in contact with the optical measuring path for the first time; and the incident portion and the reflecting surface are arranged in a discontinuous manner.

2. The sample measurement pool of claim 1, wherein the reflecting structure is a reflecting mirror, and the sample measurement pool comprises two reflecting mirrors arranged at the two ends of the reflecting cavity, respectively.

3. The sample measurement pool of claim 1, wherein the reflecting cavity is a region formed by the optical measuring path.

4. The sample measurement pool of claim 1, wherein the reflecting surface is plated with a reflecting film.

5. The sample measurement pool of claim 1, wherein the reflecting surface is a full reflecting surface.

6. The sample measurement pool of claim 1, wherein the incident portion is a light-passing surface or a light-passing hole on the reflecting structure or an incident region around the reflecting structure.

7. The sample measurement pool of claim 1, wherein the non-planar surface is a spherical surface, a cylindrical surface, a quadratic curve surface, a free-form curve surface or an aspherical surface.

8. The sample measurement pool of claim 1, wherein the waist position of the incident light is located inside the reflecting cavity.

9. The sample measurement pool of claim 1, wherein an included angle in a value range of 0°-360° is formed between the at least one reflecting structure.

10. The sample measurement pool of claim 1, wherein a protective structure is arranged on the reflecting surface, and is configured to protect the reflecting surface.

11. The sample measurement pool of claim 2, wherein the reflecting surface is a full reflecting surface.

12. The sample measurement pool of claim 2, wherein the incident portion is a light-passing surface or a light-passing hole on the reflecting structure or an incident region around the reflecting structure.

13. The sample measurement pool of claim 2, wherein an included angle in a value range of 0°-360° is formed between the at least one reflecting structure.

14. The sample measurement pool of claim 2, wherein a protective structure is arranged on the reflecting surface, and is configured to protect the reflecting surface.

\* \* \* \* \*